(12) United States Patent
Tuval

(10) Patent No.: US 11,666,314 B2
(45) Date of Patent: Jun. 6, 2023

(54) METHOD AND APPARATUS FOR CLOSING A HOLE IN CARDIAC TISSUE

(71) Applicant: Medtronic Vascular Galway, Galway (IE)

(72) Inventor: Yossi Tuval, Even Yehuda (IL)

(73) Assignee: Medtronic Vascular Galway, Galway (IE)

(*) Notice: Subject to any disclaimer, the term of this patent is extended or adjusted under 35 U.S.C. 154(b) by 791 days.

(21) Appl. No.: 16/784,629

(22) Filed: Feb. 7, 2020

(65) Prior Publication Data

US 2020/0245986 A1 Aug. 6, 2020

Related U.S. Application Data

(63) Continuation of application No. 15/354,136, filed on Nov. 17, 2016, now Pat. No. 10,575,838, which is a continuation of application No. 13/179,727, filed on Jul. 11, 2011, now Pat. No. 9,526,483.

(60) Provisional application No. 61/364,431, filed on Jul. 15, 2010.

(51) Int. Cl.
  *A61B 17/00* (2006.01)

(52) U.S. Cl.
  CPC .............. *A61B 17/0057* (2013.01); *A61B 2017/00243* (2013.01); *A61B 2017/00592* (2013.01); *A61B 2017/00597* (2013.01); *A61B 2017/00601* (2013.01); *A61B 2017/00623* (2013.01); *A61B 2017/00867* (2013.01)

(58) Field of Classification Search
  CPC ........... A61B 2017/00575; A61B 2017/00579; A61B 2017/00592; A61B 2017/00597; A61B 2017/00601; A61B 2017/00606; A61B 2017/0061; A61B 2017/00615; A61B 2017/00623; A61B 2017/00628; A61B 2017/00632; A61B 2017/00654; A61B 2017/00659

See application file for complete search history.

(56) References Cited

U.S. PATENT DOCUMENTS

| | | |
|---|---|---|
| 6,346,074 B1 | 2/2002 | Steven |
| 6,401,720 B1 | 6/2002 | Steven |
| 6,527,800 B1 | 3/2003 | McGuckin, Jr. |
| 6,978,176 B2 | 12/2005 | Lattouf |
| 7,001,398 B2 | 2/2006 | Carley |
| 7,070,618 B2 | 7/2006 | Streeter |
| 7,404,824 B1 | 7/2008 | Webler |
| 7,445,623 B2 | 11/2008 | Mialhe |
| 7,549,983 B2 | 6/2009 | Roue |

(Continued)

FOREIGN PATENT DOCUMENTS

| | | |
|---|---|---|
| EP | 1595504 A1 | 11/2005 |
| WO | 1998/47430 A1 | 10/1998 |

(Continued)

*Primary Examiner* — Martin T Ton
(74) *Attorney, Agent, or Firm* — Medler Ferro Woodhouse & Mills PLLC

(57) ABSTRACT

Aspects of the present invention provide apparatuses and methods for closing an apical hole in a heart of a subject, including a hole-closure device that includes a tissue-attachment portion configured to attach to cardiac tissue around the apical hole, and a collapsible portion coupled to the tissue-attachment portion and configured to close the hole by collapsing inwardly inside the apical hole.

20 Claims, 9 Drawing Sheets

(56) References Cited

U.S. PATENT DOCUMENTS

| | | |
|---|---|---|
| 7,635,386 B1 | 12/2009 | Gammie |
| 2002/0055772 A1* | 5/2002 | McGuckin, Jr. .......... A61F 2/82 |
| | | 623/1.24 |
| 2003/0130571 A1* | 7/2003 | Lattouf .............. A61B 17/0401 |
| | | 623/2.11 |
| 2003/0144694 A1 | 7/2003 | Chanduszko et al. |
| 2003/0153935 A1* | 8/2003 | Mialhe ............. A61B 17/12172 |
| | | 623/1.15 |
| 2003/0163191 A1 | 8/2003 | Nikolic et al. |
| 2004/0249412 A1 | 12/2004 | Snow et al. |
| 2005/0240200 A1 | 10/2005 | Bergheim |
| 2006/0058820 A1 | 3/2006 | Mialhe |
| 2006/0058871 A1 | 3/2006 | Zakay |
| 2006/0074484 A1 | 4/2006 | Huber |
| 2006/0247570 A1 | 11/2006 | Pokorney |
| 2007/0093890 A1 | 4/2007 | Eliasen |
| 2007/0112422 A1 | 5/2007 | Dehdashtian |
| 2007/0173868 A1 | 7/2007 | Bachinski et al. |
| 2007/0255399 A1 | 11/2007 | Eliasen |
| 2007/0265700 A1 | 11/2007 | Eliasen |
| 2008/0051830 A1 | 2/2008 | Eidenschink |
| 2008/0125860 A1 | 5/2008 | Webler |
| 2008/0125861 A1 | 5/2008 | Webler |
| 2009/0043382 A1 | 2/2009 | Maurer |
| 2009/0048668 A1 | 2/2009 | Wilson |
| 2009/0240326 A1 | 9/2009 | Wilson |
| 2009/0287183 A1 | 11/2009 | Bishop |
| 2010/0016885 A1 | 1/2010 | Eidenschink |
| 2010/0168778 A1 | 7/2010 | Braido |
| 2010/0274091 A1 | 10/2010 | Rothstein |
| 2012/0083832 A1* | 4/2012 | Delaloye ............ A61B 17/0057 |
| | | 606/213 |
| 2012/0253386 A1* | 10/2012 | Rowe ..................... A61B 17/02 |
| | | 606/213 |
| 2014/0163609 A1* | 6/2014 | Solem ............. A61B 17/12113 |
| | | 606/213 |

FOREIGN PATENT DOCUMENTS

| | | |
|---|---|---|
| WO | 2004/087235 A2 | 10/2004 |
| WO | 2008/024491 A1 | 2/2008 |
| WO | 2008/141322 A1 | 11/2008 |
| WO | 2008/141325 A1 | 11/2008 |
| WO | 2009/002548 A1 | 12/2008 |
| WO | 2009/100198 A2 | 8/2009 |
| WO | 2009/127973 A2 | 10/2009 |

* cited by examiner

METHOD AND APPARATUS FOR CLOSING A HOLE IN CARDIAC TISSUE

CROSS-REFERENCE TO RELATED APPLICATION

This application is a continuation of prior U.S. Pat. No. 15,354,136, filed Nov. 17, 2016, now U.S. Pat. No. 10,575,838, which is a continuation of U.S. application Ser. No. 13/179,727, filed Jul. 11, 2011, now U.S. Pat. No. 9,526,483, which claims the benefit of U.S. Appl. No. 61/364,431, filed Jul. 15, 2010, which are incorporated by reference herein in their entirety.

BACKGROUND OF THE INVENTION

Field of the Invention

Some applications of the present invention generally relate to medical apparatus. Specifically, some applications of the present invention relate to apparatuses and methods for closing an artificial hole in a subject's body.

Background

The apex of the heart is the lowest point of the surface of the heart, at the bottom of the left ventricle. In minimally-invasive cardiac surgery, a transapical approach allows tools to be inserted into the subject's heart via a hole in the apex of the heart. For example, the transapical approach may be used in aortic valve implantation, left ventricular bypass, and aortic cannulation procedures.

BRIEF SUMMARY OF THE INVENTION

For some applications of the present invention, apparatuses and methods are provided for closing a hole in the apex of a subject's heart. An apical-hole closure device is typically placed inside the hole during (or prior to, or subsequent to) a cardiac procedure in which tissue inside the subject's heart is accessed transapically via the hole in the apex. The apical-hole closure device is inserted into the apical hole. A tissue-attachment portion of the apical-hole closure device becomes attached to cardiac tissue around the apical hole, for example, by hooks of the tissue-attachment portion becoming hooked to the tissue. A collapsible portion of the apical-hole closure device is coupled to the tissue-attachment portion. Subsequent to attachment of the tissue-attachment portion to the cardiac tissue around the hole, the collapsible portion collapses inwardly into a collapsed state thereof, inside the apical hole. The collapse of the collapsible portion, while the tissue-attachment portion is coupled to the tissue around the hole, typically causes the tissue around the hole to at least partially close the hole. Alternatively, the hole does not close, but the collapse of the collapsible portion prevents the flow of blood through the hole.

Typically, the apical-hole closure device is inserted into the apical hole while the closure device is disposed around a delivery device, such as an introducer. While the closure device is around the delivery device, the collapsible portion of the apical-hole closure device is prevented from collapsing, by the delivery device. Withdrawal of the delivery device from inside the device facilitates the collapse of the collapsible portion.

For some applications, sealing material is disposed inside the apical-closure device. When the device is in the collapsed state thereof inside the apical hole, the sealing material seals the center of the device, thereby sealing the apical hole.

There is therefore provided, in accordance with some applications of the present invention, an apparatus for closing an apical hole in a heart of a subject, including a hole-closure device that includes a tissue-attachment portion configured to become attached to cardiac tissue around the apical hole and a collapsible portion, coupled to the tissue-attachment portion, that is configured to be in an expanded state during insertion of the device into the apical hole, and to close the hole by collapsing inwardly into a collapsed state thereof, inside the apical hole.

For some applications, the apparatus further includes a sheath configured to be removably disposed around the collapsible structure and the tissue-attachment portion, and the tissue-attachment portion is configured to be in a first state thereof when the sheath is disposed around the tissue-attachment portion, and in a second state thereof when the sheath is not disposed around the tissue-attachment portion.

For some applications, the apparatus further includes a sealing material disposed inside the collapsible portion, configured to form a seal within the collapsible portion when the collapsible portion is in the collapsed state thereof.

For some applications, the tissue-attachment portion includes a plurality of tissue-attachment portions.

For some applications, the tissue-attachment portion includes proximal and distal tissue-attachment portions disposed respectively at proximal and distal ends of the hole-closure device, and configured, respectively to become coupled to extracardiac and intracardiac tissue of the subject around the hole.

For some applications, the tissue-attachment portion includes a plurality of tissue-attachment elements.

For some applications, the tissue-attachment elements include hooks configured to become hooked to the cardiac tissue around the apical hole.

For some applications, the apparatus further includes a delivery device, and the hole-closure device is configured to be disposed around the delivery device during insertion of the hole-closure device into the apical hole, the delivery device is configured to prevent the collapsible portion from collapsing while the hole-closure device is disposed around the delivery device, and the delivery device is configured to facilitate the collapse of the collapsible portion by being withdrawn from inside the hole-closure device.

For some applications, the delivery device is configured to be used for a transapical procedure that is conducted via the apical hole, while the hole-closure device is disposed around the delivery device.

For some applications, the delivery device includes a catheter, configured to facilitate passage therethrough of an instrument that is used in the transapical procedure.

There is further provided, in accordance with some applications of the present invention, a method for closing an apical hole in a heart of a subject, including inserting a hole-closure device into the apical hole, while a collapsible portion of the device is in an expanded state thereof, attaching to cardiac tissue around the apical hole, a tissue-attachment portion of the device, and closing the apical hole, by collapsing the collapsible portion of the device into a collapsed state thereof, while the collapsible portion is inside the apical hole.

For some applications, attaching the tissue-attachment portion of the device to the cardiac tissue around the apical hole includes removing a sheath from around the tissue-attachment portion.

For some applications, closing the hole includes sealing the hole by collapsing the collapsible portion of the device, there being a sealing material disposed inside the collapsible portion.

For some applications, attaching the tissue-attachment portion of the device to the cardiac tissue around the apical hole includes attaching a plurality of tissue-attachment portions of the device to the cardiac tissue around the apical hole.

For some applications, attaching the tissue-attachment portions of the device to the cardiac tissue around the apical hole includes attaching a proximal tissue-attachment portion disposed at a proximal end of the device to extracardiac tissue of the subject around the hole, and attaching a distal tissue-attachment portion disposed at a distal end of the device to intracardiac tissue of the subject around the hole.

For some applications, attaching the tissue-attachment portions of the device to the cardiac tissue around the apical hole includes attaching a plurality of tissue-attachment elements of the device to the cardiac tissue around at least one end of the hole.

For some applications, attaching the tissue-attachment elements to the cardiac tissue includes hooking hooks to the cardiac tissue around the apical hole.

For some applications, inserting the hole-closure device into the apical hole includes inserting a delivery device into the hole, the hole-closure device being disposed around the delivery device, and collapsing the collapsible portion of the device includes removing the delivery device from inside the hole-closure device.

For some applications, the method further includes using the delivery device to facilitate a transapical procedure that is conducted via the apical hole, while the hole-closure device is disposed around the delivery device.

For some applications, using the delivery device includes facilitating passage therethrough of an instrument that is used in the transapical procedure.

There is additionally provided, in accordance with some applications of the present invention, an apparatus, including a tool configured to be inserted through an artificial hole in a subject's body, and a hole-closure device configured to be disposed around the tool during the insertion of the tool into the hole, the hole-closure device including a tissue-attachment portion configured to attach the hole-closure device to tissue of the subject in a vicinity of the hole and to maintain the attachment even after the tool is removed from the hole, and a collapsible portion configured to close the hole by automatically collapsing inwardly inside the hole, upon removal of the tool from the hole.

For some applications, the tool includes a delivery device.

There is further provided, in accordance with some applications of the present invention, apparatus for closing a hole in tissue of a subject, including a hole-closure device that includes a collapsible structure that is configured to collapse from a first configuration to a second configuration, a tissue-attachment portion coupled to the collapsible structure, and configured to attach the collapsible portion to tissue around the hole, and a sheath configured to be removably disposed around the collapsible structure and the tissue-attachment portion, the tissue-attachment portion being configured to be in a first state thereof when the sheath is disposed around the tissue-attachment portion, and in a second state thereof when the sheath is not disposed around the tissue-attachment portion.

For some applications, the device is configured to close the hole by the collapsible structure collapsing from the first configuration to the second configuration while the collapsible portion is coupled to the tissue around the hole.

For some applications, the tissue-attachment portion includes a plurality of tissue-attachment portions.

For some applications, the tissue-attachment portion includes proximal and distal tissue-attachment portions disposed respectively at proximal and distal ends of the collapsible structure.

For some applications, the tissue-attachment portion includes a plurality of tissue-attachment elements.

For some applications, the tissue-attachment elements include hooks configured to become hooked to the tissue.

For some applications, the tissue-attachment portion is configured to be in a straightened state thereof when the sheath is disposed around the tissue-attachment portion, and in a curved state thereof when the sheath is not disposed around the tissue-attachment portion.

For some applications, the tissue-attachment portion, by assuming the curved state thereof, is configured to become attached to the tissue around the hole.

For some applications, the tissue-attachment portion includes a shape-memory alloy that is configured to assume the curved state thereof when the tissue-attachment portion is not constrained.

The present invention will be more fully understood from the following detailed description of embodiments thereof, taken together with the drawings.

DETAILED DESCRIPTION OF THE INVENTION

Figure 1:
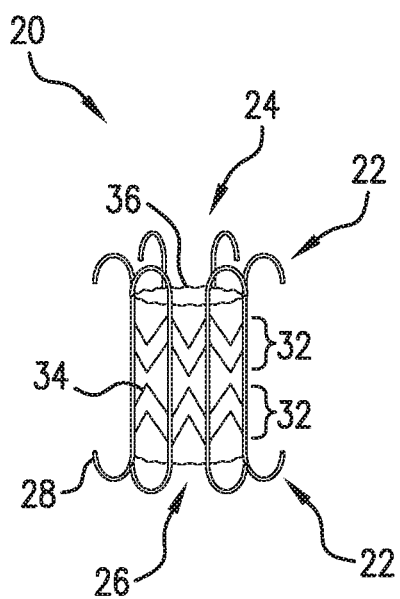
FIG. 1 is a schematic illustration of an apical-hole closure device, in accordance with some exemplary embodiments of the present invention.

Reference is now made to FIG. 1, which is a schematic illustration of an apical-hole closure device 20, in accordance with some exemplary embodiments of the present invention. The apical-hole closure device is typically used to close an artificial hole in the apex of a subject's heart due to a transapical procedure, such as an aortic valve implantation procedure, a left ventricular bypass procedure, an aortic cannulation procedure, and/or a different transapical procedure.

Apical-hole closure device 20 includes at least one tissue-attachment portion 22. For example, as shown in FIG. 1, apical-hole closure device 20 may include distal and proximal tissue-attachment portions 22 disposed respectively at distal end 24 and proximal end 26 of device 20. For some exemplary embodiments, as shown, tissue-attachment portion 22 includes a plurality of tissue-attachment elements 28, such as hooks, pins, adhesive portions, and/or other elements that are configured to become attached to tissue of the subject around the apical hole.

Apical-hole closure device 20 additionally includes a collapsible portion 32 that is coupled to tissue-attachment portion 22, and that has expanded and contracted states thereof, as described in further detail herein. For some exemplary embodiments, collapsible portion 32 includes collapsible members 34 that couple tissue-attachment elements 28 to each other, as shown. For example, collapsible members 34 may have a saw-tooth shape (as shown), or a sinusoidal shape (not shown), and/or another shape that facilitates the collapse of the collapsible portion from an expanded state to a collapsed state thereof.

Typically, collapsible portion 32 includes a shape-memory material (e.g., nitinol). For some applications, the shape-memory material is shaped such that when unconstrained, it assumes the shape that it has in the collapsed state. During insertion of apical-hole closure device 20 into the apical hole, collapsible portion 32 is stretched by a delivery device 40, as described herein. When delivery device 40 is withdrawn from apical-hole closure device 20 (i.e., removed from inside collapsible portion 32), collapsible portion 32 recollapses into the collapsed state. Alternatively, the shape-memory material is configured such that collapsible portion 32 is in the expanded state at a temperature which is not 37 C. Shape-memory techniques are used to configure collapsible portion 32 to change to the collapsed state, when collapsible portion 32 is allowed to reach 37 C, when it is disposed inside the apical hole.

For some exemplary embodiments, a sealing material 36 is disposed inside collapsible portion 32. For example, sealing material 36 may include a supple biocompatible material (such as woven or knitted polyester, biological tissue (e.g., tissue of the pericardium), or expanded polytetrafluoroethylene (ePTFE)). The material is typically folded inside collapsible portion 32, such that when collapsible portion 32 is in the collapsed state thereof, the sealing material seals the inside of apical-hole closure device 20, as described herein.

Figure 2:
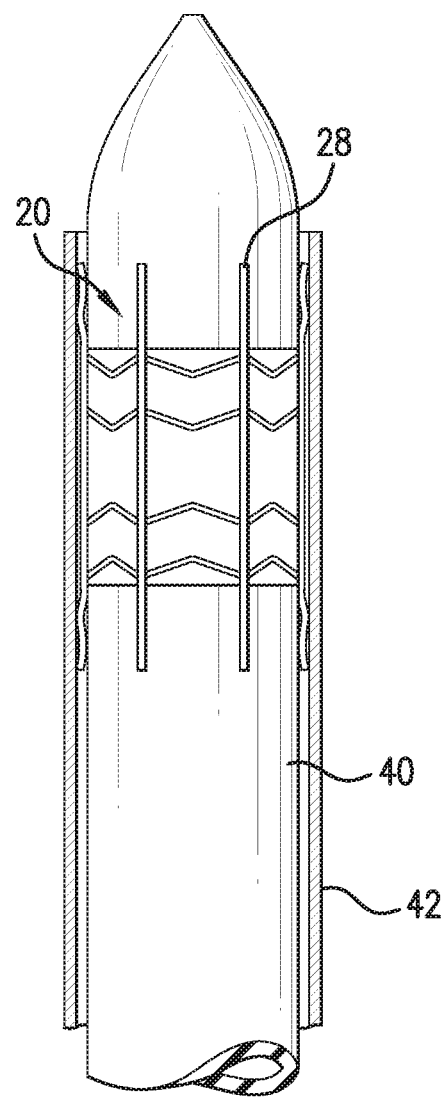
FIG. 2 is a schematic illustration of the apical-hole closure device disposed around a delivery device, in accordance with some exemplary embodiments of the present invention.

Reference is now made to FIG. 2, which is a schematic illustration of apical-hole closure device 20 disposed around delivery device 40, in accordance with some exemplary embodiments of the present invention. In accordance with respective exemplary embodiments, delivery device 40 is a dedicated delivery device for delivering apical-hole closure device 20 to the apical hole, or is a device that is additionally used for a part of the transapical procedure other than the delivery of apical-hole closure device 20. For example, delivery device 40 may be a catheter by means of which tools are inserted into the subject's heart during a transapical procedure. For some exemplary embodiments, delivery device 40 is used to insert apical-hole closure device 20 into the apical hole prior to or subsequent to the transapical procedure.

A sheath 42 is typically disposed around apical-hole closure device 20 during insertion of apical-hole closure device 20 into the apical hole. Sheath 42 constrains tissue-attachment elements 28 of apical-hole closure device 20 during insertion of apical-hole closure device 20 into the hole.

Figure 3:
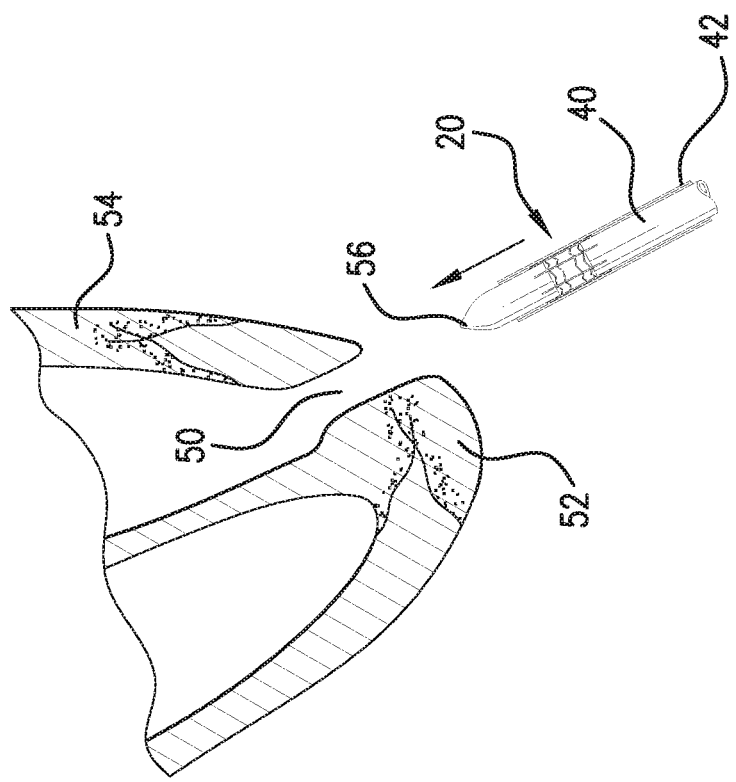
FIG. 3 is a schematic illustration of the delivery device being advanced toward the apex of the heart, in accordance with some exemplary embodiments of the present invention.

Reference is now made to FIG. 3, which is a schematic illustration of delivery device 40 being advanced toward a hole 50 at apex 52 of a heart 54, in accordance with some exemplary embodiments of the present invention. For some exemplary embodiments, distal end 56 of delivery device 40 is used to incise the subject's heart 54 and to create hole 50 in apex 52 of heart 54. Alternatively or additionally, a cutting tool is inserted via delivery device 40 in order to incise apex 52 of heart 54, and the distal end of delivery device 40 dilates hole 50. Further alternatively or additionally, delivery device 40 is inserted into hole 50 subsequent to apex 52 having been incised during a transapical procedure.

Figure 4:
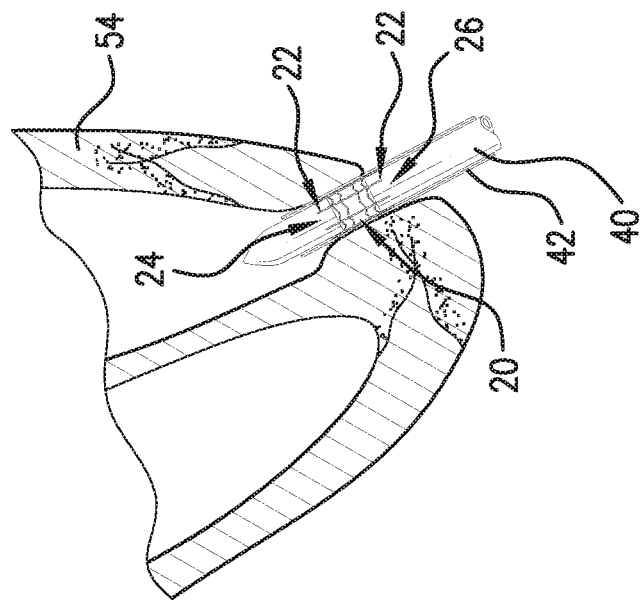
FIG. 4 is a schematic illustration of the delivery device inserted inside an apical hole, the apical-hole closure device being disposed around the delivery device, in accordance with some exemplary embodiments of the present invention.

Reference is now made to FIG. 4, which is a schematic illustration of delivery device 40 inserted within apical hole 50, with apical-hole closure device 20 disposed around delivery device 40, in accordance with some exemplary embodiments of the present invention. As can be seen, the apical-hole closure device 20 is preferably positioned such that tissue-attachment elements 28 are aligned with a proximal and a distal side of apical hole 50. It is understood that although tissue-attachment elements 28 are shown as tines, in some embodiments other types of tissue-attachment elements are alternatively or additionally used, including, for example, adhesive, sutures, screws, pins, or staples.

Figure 5:
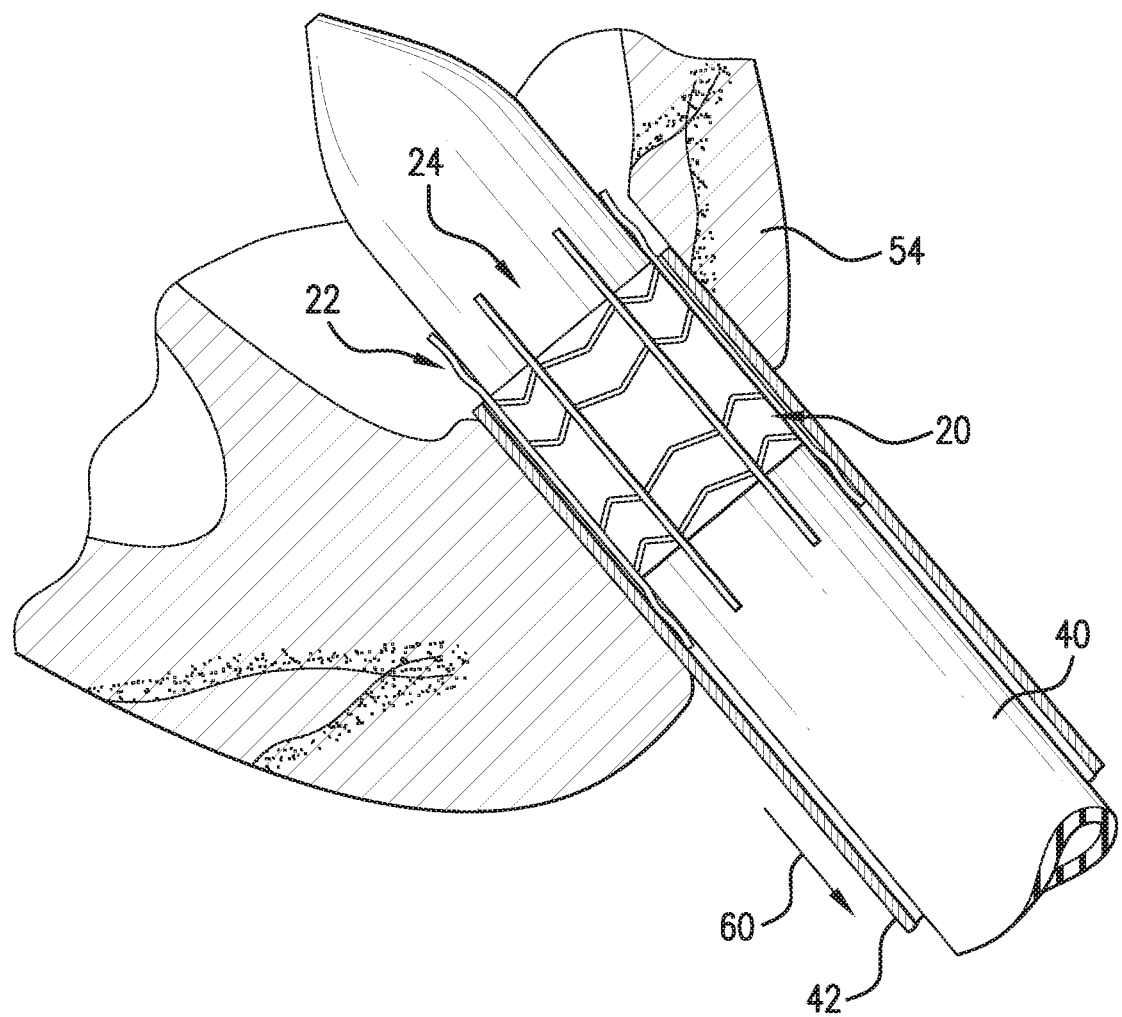
FIG. 5 is a schematic illustration of a sheath being withdrawn from around the distal end of the apical-hole closure device, in accordance with some exemplary embodiments of the present invention.
Figure 6:
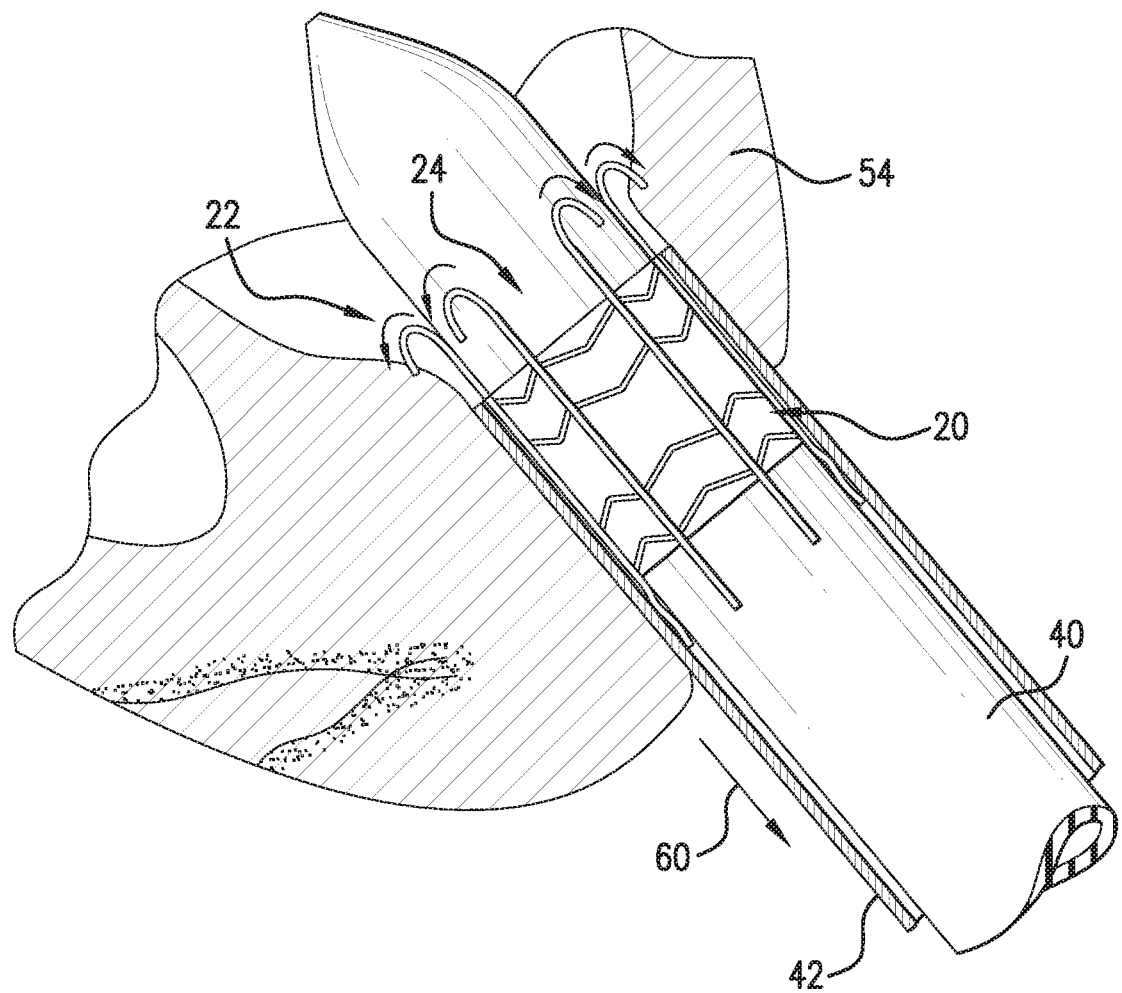
FIG. 6 is a schematic illustration of distal tissue-attachment elements of the apical-hole closure device becoming attached to cardiac tissue around the intracardiac end of the apical hole, in accordance with some exemplary embodiments of the present invention.

Reference is now made to FIGS. 5 and 6, which are schematic illustrations of sheath 42 being withdrawn from around distal end 24 of apical-hole closure device 20, in accordance with some exemplary embodiments of the present invention. For some exemplary embodiments, once apical-hole closure device 20 is positioned inside apical hole 50, sheath 42 is withdrawn from around distal end 24 of apical-hole closure device 20, in the direction of arrow 60. In response to sheath 42 being withdrawn, tissue-attachment portion 22 at distal end 24 of apical-hole closure device 20 becomes attached to cardiac tissue around apical hole 50. For example, tissue-attachment elements 28 of tissue-attachment portion 22 may include a shape-memory alloy (such as nitinol). While tissue-attachment elements 28 are inside sheath 42, sheath 42 constrains tissue-attachment elements 28 in a non-attachment configuration (e.g., straightened). In response to sheath 42 being withdrawn from around tissue-attachment elements 28, tissue-attachment elements 28 curve in an attachment configuration (e.g., defining a U-shape) and become attached to tissue around apical hole 50. Although the illustrated embodiment contains six tissue-attachment elements 28, it is understood that greater than six or less than six tissue-attachment elements 28 can be used.

In regard to an embodiment using, for example, adhesive as tissue-attachment elements 28, the withdrawal of sheath 42 from around tissue attachment elements 28 can expose the adhesive to tissue around apical hole 50, thereby causing apical-hole closure device 20 to become attached to tissue around apical hole 50.

In regard to an embodiment using, for example, pins or staples as tissue-attachment elements 28, tissue-attachment elements 28 can be constrained in a non-attachment configuration by sheath 42, and the withdrawal of sheath 42 from around tissue attachment elements 28 can allow tissue-attachment elements 28 to naturally move to a non-constrained state, which coincides with an attachment configuration. This movement can cause tissue-attachment elements 28 to attach to tissue around apical hole 50 (e.g., pins or staple tines can extend into and affix to the tissue), thereby causing apical-hole closure device 20 to become attached to tissue around apical hole 50.

Figure 7:
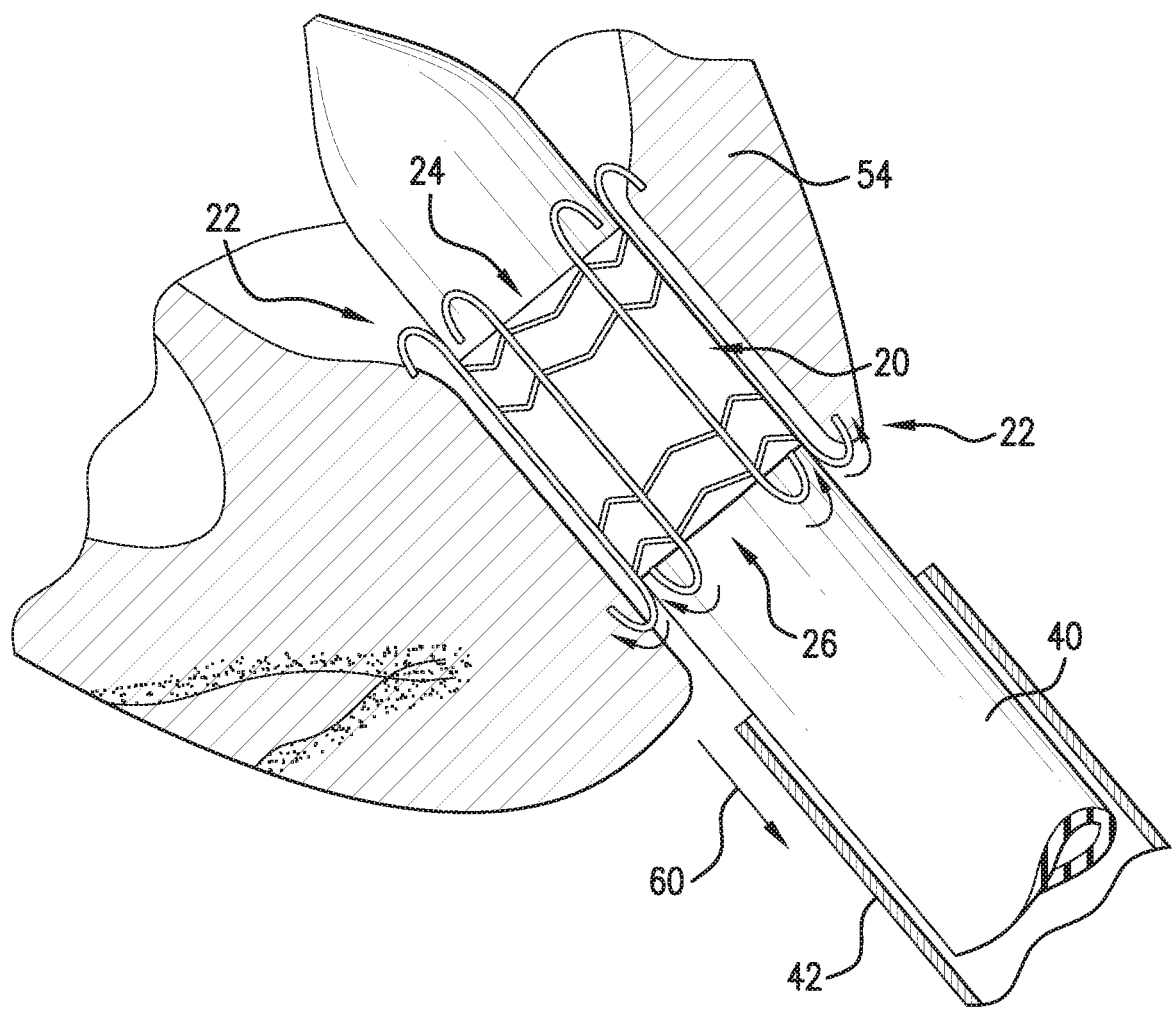
FIG. 7 is a schematic illustration of proximal tissue-attachment elements of the apical-hole closure device becoming attached to cardiac tissue around the extracardiac end of the apical hole, in accordance with some exemplary embodiments of the present invention.

Reference is now made to FIG. 7, which is a schematic illustration of sheath 42 having been withdrawn from around proximal end 26 of apical-hole closure device 20, in accordance with some exemplary embodiments of the present invention. For some exemplary embodiments, subsequent to the withdrawal of sheath 42 from distal end 24 of apical-hole closure device 20, sheath 42 is withdrawn from proximal end 26 of device 20, in the direction of arrow 60. In response to sheath 42 being withdrawn, tissue-attachment portion 22 at proximal end 26 of apical-hole closure device 20 becomes attached to cardiac tissue around apical hole 50. For example, tissue-attachment elements 28 at proximal end 26 of apical-hole closure device 20 may function in a similar manner to tissue-attachment elements 28 at distal end 24 of apical-hole closure device 20, as described with reference to FIGS. 5-6. Although the illustrated embodiment includes hooks at both distal end 24 and proximal end 26 of apical-hole closure device 20, it is understood that tissue-attachment elements 28 on the proximal end may be of a different type different from tissue attachment elements 28 on the distal end, and that more than one type of tissue-attachment element 28 may be on the same end.

As shown, for some exemplary embodiments, apical-hole closure device 20 includes tissue-attachment portions 22 at distal end 24 and at proximal end 26 of apical-hole closure device 20. Apical-hole closure device 20 is shaped such that when sheath 42 is withdrawn from apical-hole closure device 20, distal tissue-attachment portion 22 becomes attached to intracardiac tissue around apical hole 50, and the proximal tissue-attachment portion 22 becomes attached to extracardiac tissue around apical hole 50. Alternatively, apical-hole closure device 20 is shaped such that one or both of the tissue-attachment portions 22 become attached to a different portion of the subject's tissue. For example, apical-hole closure device 20 may be shaped such that one or both of the tissue-attachment portions 22 becomes attached to tissue of the myocardium that surrounds a central portion of hole 50 (i.e., a portion of hole 50 that is not at the intracardiac or the extracardiac end of hole 50). Further alternatively, apical-hole closure device 20 includes only one tissue-attachment portion 22, disposed at proximal end 26 or distal end 24 of apical-hole closure device 20, or in a different region of apical-hole closure device 20. For example, apical-hole closure device 20 may include a single tissue-attachment portion 22, disposed along part or the entire length of device 20 (e.g., an adhesive surrounded by a sheath, or a plurality of mechanical tissue-engagement elements as described herein (for example, hooks or barbs)). Still further alternatively, apical-hole closure device 20 includes more than two tissue-attachment portions 22.

Figure 8:
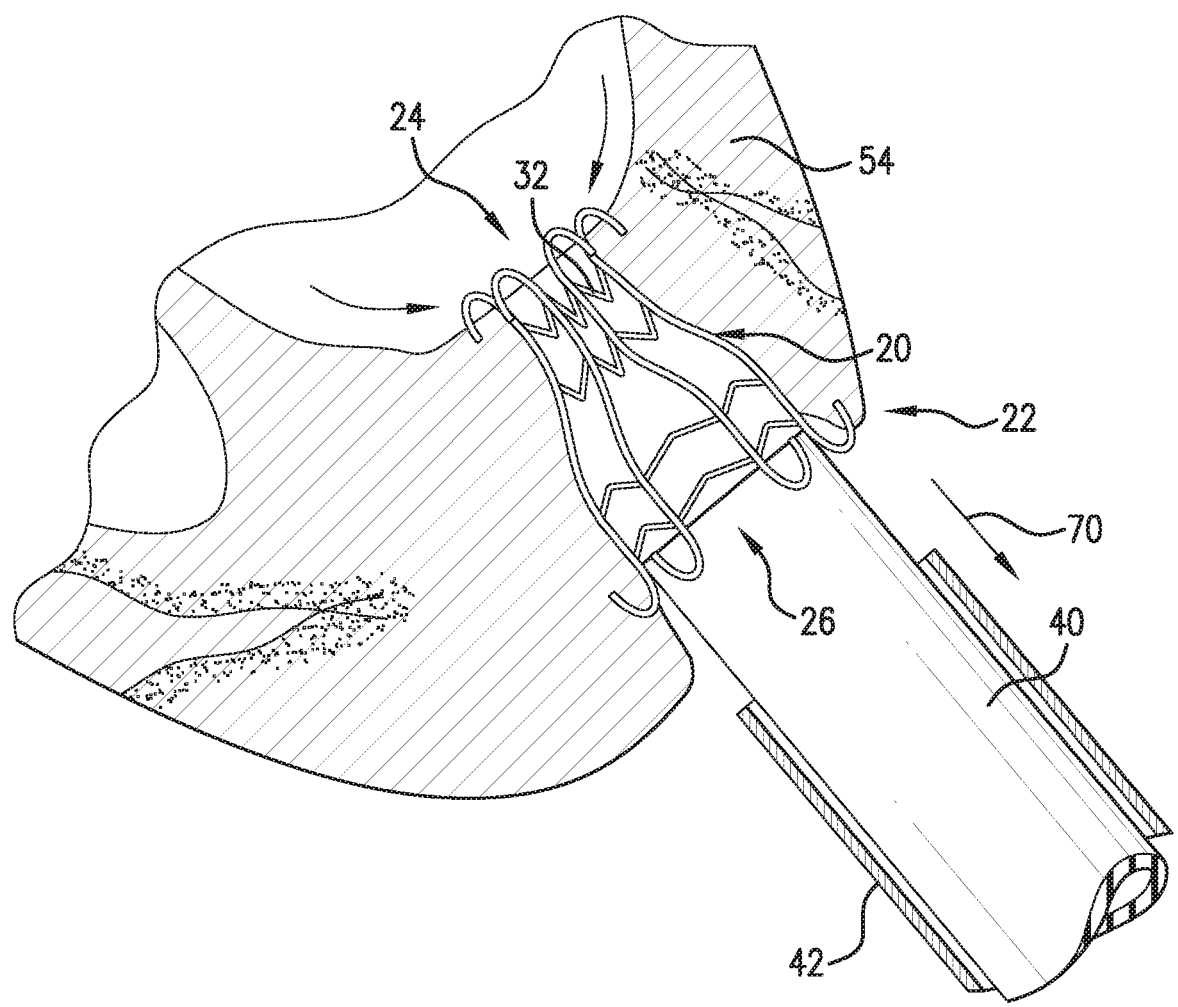
FIG. 8 is a schematic illustration of the insertion device being withdrawn from the apical hole subsequent to the tissue-attachment elements becoming attached to the cardiac tissue, in accordance with some exemplary embodiments of the present invention.
Figure 9:
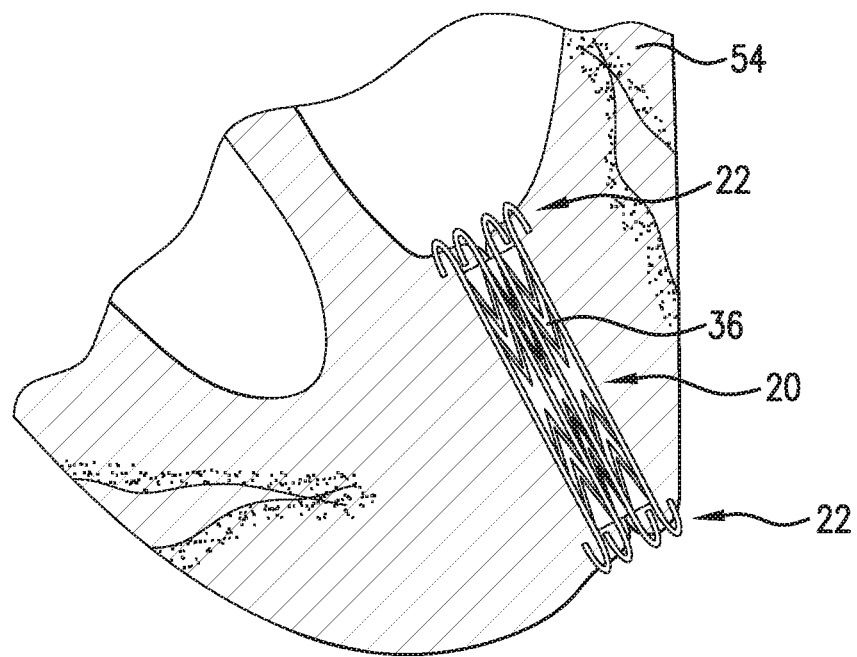
FIG. 9 is a schematic illustration of the apical-hole closure device in a collapsed state thereof, subsequent to the withdrawal of the insertion device from the apical hole, in accordance with some exemplary embodiments of the present invention.

Reference is now made to FIG. 8, which is a schematic illustration of insertion device 40 being withdrawn from apical hole 50 subsequent to tissue-attachment portions 22 becoming attached to cardiac tissue, in accordance with some exemplary embodiments of the present invention. Typically, as insertion device 40 is withdrawn from the distal end of apical hole 50, in the direction of arrow 70, collapsible portion 32 at distal end 24 of apical-hole closure device 20 collapses. As insertion device 40 continues to be withdrawn in the direction of arrow 70, collapsible portion 32 at proximal end 26 of apical-hole closure device 20 collapses (FIG. 9). Since tissue-attachment portions 22 of the apical-hole closure device are attached to tissue around hole 50, the collapse of collapsible portion 32 results in the tissue that surrounds hole 50 being pulled toward the center of hole 50, thereby at least partially closing hole 50.

Reference is now made to FIG. 9, which is a schematic illustration of apical-hole closure device 20 in a collapsed state thereof, subsequent to the withdrawal of insertion device 40, in accordance with some exemplary embodiments of the present invention. Collapsible portion 32 typically causes apical-hole closure device 20 to collapse toward the center of apical hole 50. Since apical-hole closure device 20 is attached to myocardial tissue via tissue-attachment elements 28, the collapse of apical-hole closure device 20 pulls the myocardial tissue around hole 50 toward the center of hole 50. For some exemplary embodiments, the myocardial tissue naturally contracts toward the center of hole 50 following removal of insertion device 40 from hole 50, and apical-hole closure device 20 assists the natural process.

Typically, sealing material 36 is disposed in the center of apical-hole closure device 20, and seals apical hole 50 due to the collapse of apical-hole closure device 20. For some exemplary embodiments, a different element is used to seal the center of device 20. For example, a valve may be disposed in the center of device 20, the valve being configured to close upon the removal of insertion device 40 from inside apical-hole closure device 20. Sealing material 36 typically seals apical-hole closure device 20, thereby sealing apical hole 50.

Figure 10:
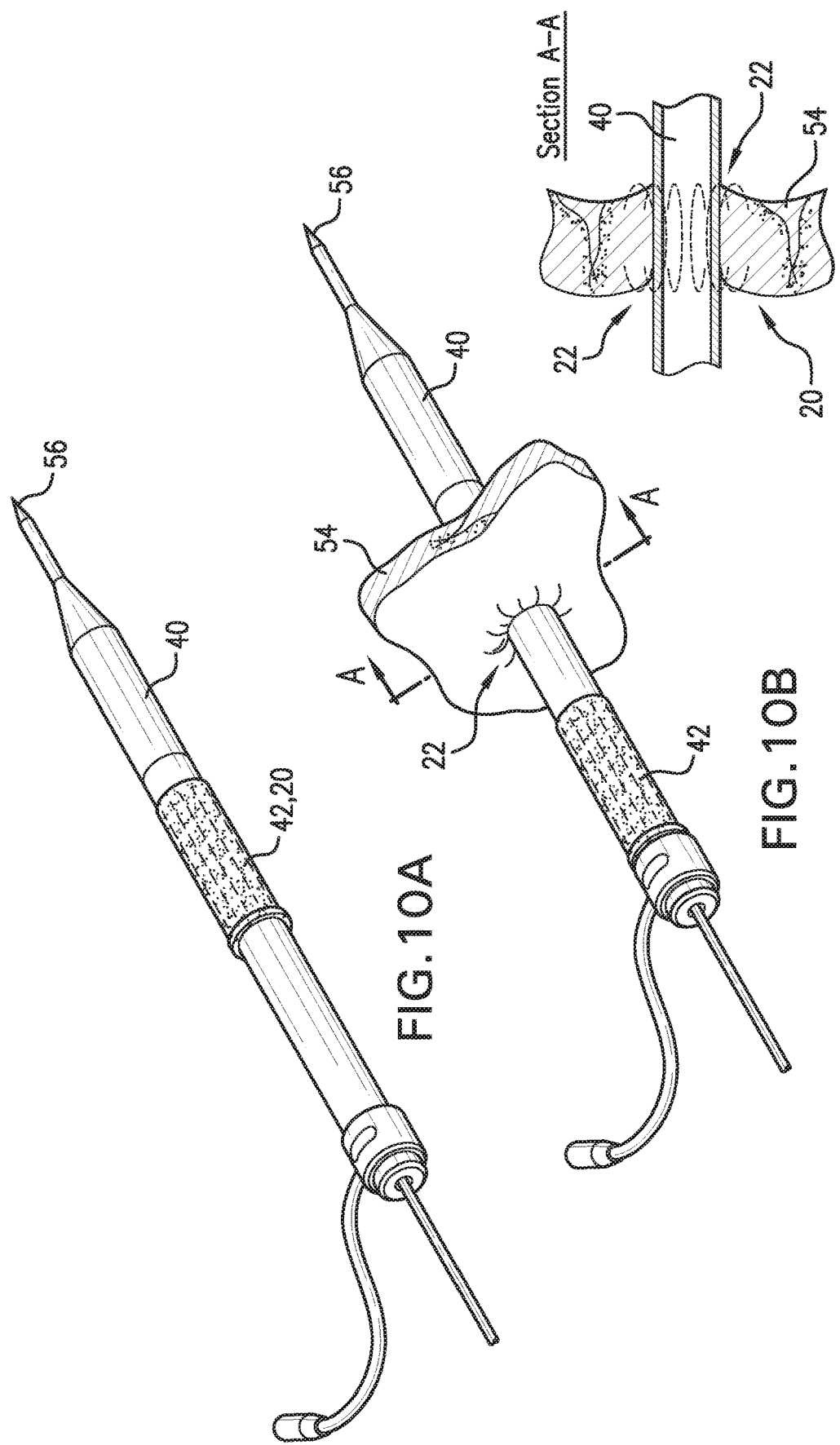
FIG. 10A is a schematic illustration of the apical-hole closure device on a delivery device while a sheath is disposed around the apical-hole closure device, in accordance with some exemplary embodiments of the present invention.
FIG. 10B is a schematic illustration of the apical-hole closure device on a delivery device subsequent to the sheath having been withdrawn from around the apical-hole closure device.
FIG. 10C is an enlarged cross-sectional schematic illustration of a portion of the schematic illustration of FIG. 10B.

Reference is now made to FIG. 10A, which is a schematic illustration of apical-hole closure device 20 on delivery device 40 while sheath 42 is disposed around apical closure device 20, FIG. 10B, which is a schematic illustration of apical-hole closure device 20 on delivery device 40 subsequent to sheath 42 having been withdrawn from around apical-hole closure device 20, and FIG. 10C, which is an enlarged cross-sectional schematic illustration of a portion of the schematic illustration of FIG. 10B. FIG. 10B shows tissue-attachment portion 22 having become attached to the myocardial tissue of heart 54 around hole 50 in the tissue, due to the removal of sheath 42 from around apical-hole closure device 20. It is noted that, for illustrative purposes, FIG. 10B does not show certain portions of apical-hole closure device 20, such as collapsible portion 32.

Figure 11:
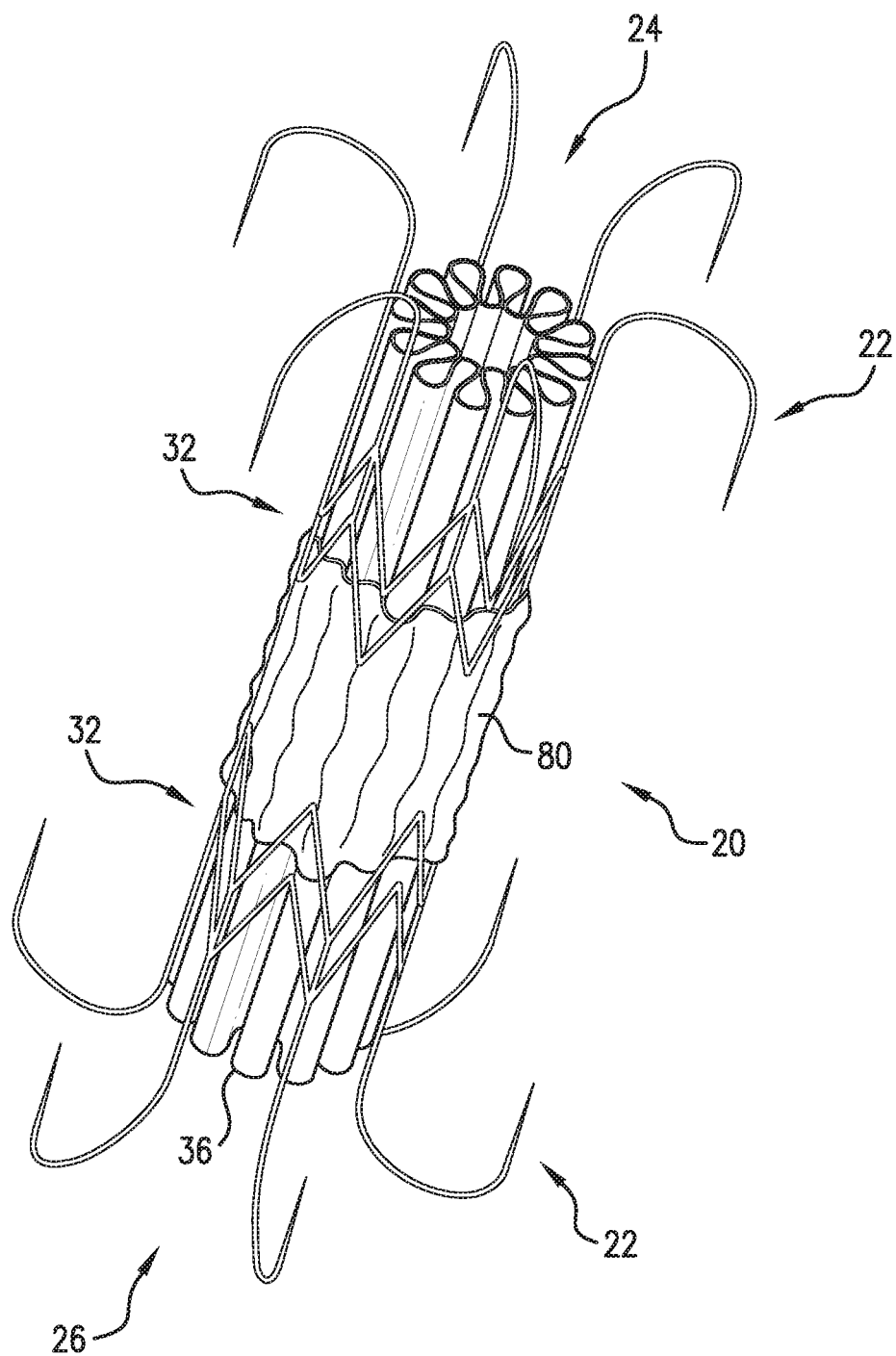
FIG. 11 is a schematic illustration of an apical-closure device that includes a flexible material in a central portion thereof, in accordance with some exemplary embodiments of the present invention.

Reference is now made to FIG. 11, which is a schematic illustration of apical-hole closure device 20, including a flexible central portion 80, made of flexible material, in accordance with some exemplary embodiments of the present invention. For some exemplary embodiments, there are proximal and distal collapsible portions 32 toward the distal and proximal ends 24 and 26 of apical-hole closure device 20. Proximal and distal collapsible portions 32 facilitate closure of the extracardiac and intracardiac ends of apical hole 50, in accordance with the techniques described herein. In between proximal and distal collapsible portions 32, there is flexible central portion 80, and there is no collapsible portion disposed around flexible central portion 80. Flexible central portion 80 seals the central region of apical hole 50 (i.e., the region of apical hole 50 that is between extracardiac and intracardiac ends of hole 50), even in the absence of a collapsible portion at the central region, due to contraction of the cardiac tissue at the central region of hole 50, around flexible central portion 80. For some exemplary embodiments, flexible central portion 80 is the same material as (and is optionally coupled to) sealing material 36. Alternatively, flexible central portion 80 is different from sealing material 36 (as shown). For example, flexible central portion 80 may be a supple biocompatible material (such as woven or knitted polyester, biological tissue (e.g., tissue of the pericardium), or ePTFE)

Although exemplary embodiments have been described herein for closing a hole in the apex of a subject's heart, the scope of the present invention includes the application of the apparatus and methods described herein to close any hole in a subject's body. For example, the hole-closure device described herein may be used to close holes resulting from other types of surgery, and/or bullet holes.

For some applications, techniques and apparatus described in the present patent application are combined with techniques and apparatus described in U.S. patent application Ser. No. 12/750,829, filed Mar. 21, 2010 to Rothstein et al., entitled "Auto-Closure Apical Access Positioner Device and Method", which is incorporated herein in its entirety by reference thereto.

It is noted that in transapical procedures, a hole is typically made at an apical site that is superior and lateral to the lowest point of the subject's heart (i.e., the anatomical apex of the heart). Therefore, the apical-hole closure device described herein is typically used to close apical holes that are in the vicinity of the anatomical apex of the heart, but not necessarily at the anatomical apex of the heart. Nevertheless, the scope of the present invention includes using the apical closure device to close an apical hole that is located at the anatomical apex of the heart. The term "apical hole" as used in the present application should be interpreted as including holes at the anatomical apex of the heart, as well as holes that are in the vicinity of the anatomical apex of the heart, but not necessarily at the anatomical apex of the heart.

It will be appreciated by persons skilled in the art that the present invention is not limited to what has been particularly shown and described herein. Rather, the scope of the present invention includes both combinations and subcombinations of the various features described herein, as well as variations and modifications thereof that are not in the prior art, which would occur to persons skilled in the art upon reading the foregoing description.

What is claimed is:

1. A method for closing a hole in cardiac tissue comprising:
   inserting a hole-closure device into the hole, while a collapsible portion of the hole-closure device is in an expanded state, wherein inserting the hole-closure device into the hole comprises inserting a delivery device into the hole, the hole-closure device being disposed around the delivery device such that the collapsible portion is held in the expanded state thereby;
   attaching a tissue-attachment portion of the hole-closure device to cardiac tissue around the hole; and
   closing the hole, by collapsing the collapsible portion of the hole-closure device into a collapsed state, wherein withdrawing the delivery device from the collapsible portion of the hole-closure device causes the collapsible portion to assume the collapsed state from the expanded state,
   wherein collapsing the collapsible portion causes the tissue-attachment portion, which extends therefrom, to draw the cardiac tissue together to close the hole.

2. The method of claim 1, wherein attaching the tissue-attachment portion of the hole-closure device to the cardiac tissue around the hole comprises removing a sheath of the delivery device from around the tissue-attachment portion.

3. The method of claim 1, wherein the collapsible portion includes a sealing material disposed in an interior thereof and wherein collapsing the collapsible portion causes the sealing material to seal a center of the hole-closure device.

4. The method of claim 1, wherein attaching the tissue-attachment portion further comprising attaching a plurality of tissue-attachment portions of the hole-closure device to the cardiac tissue around the hole.

5. The method of claim 1, wherein attaching the tissue-attachment portion of the hole-closure device to the cardiac tissue around the hole comprises attaching each of a proximal tissue-attachment portion, disposed at a proximal end of the collapsible portion of the hole-closure device, and a distal tissue-attachment portion, disposed at a distal end of the collapsible portion of the hole-closure device, to the cardiac tissue on respective ends of the hole.

6. The method of claim 1, wherein attaching the tissue-attachment portion of the hole-closure device to the cardiac tissue around the hole comprises attaching a plurality of tissue-attachment elements of the hole-closure device to the cardiac tissue around at least one end of the hole.

7. The method of claim 1, wherein the tissue-attachment portion comprises a plurality of hooks and attaching the tissue-attachment portion of the hole-closure device to the cardiac tissue comprises hooking the plurality of hooks to the cardiac tissue around the hole.

8. The method of claim 1, further comprising using the delivery device for a medical procedure conducted via the hole, while the hole-closure device is disposed around the delivery device.

9. The method of claim 8, wherein using the delivery device for a medical procedure comprises passing an instrument therethrough that is for use in the medical procedure.

10. The method of claim 8, wherein the delivery device comprises
    a shaft configured to maintain the collapsible portion of the hole-closure device in the expanded state by extending therethrough; and
    a sheath configured to be removably disposed around the tissue-attachment portion of the hole-closure device and to maintain the tissue-attachment portion in a non-attachment configuration when the tissue-attachment portion is disposed therein.

11. The method of claim 10, further comprising withdrawing the sheath from around the tissue-attachment portion to thereby permit the tissue-attachment portion to return to an attachment configuration for attaching the tissue-attachment portion of the hole-closure device to the cardiac tissue around the hole.

12. The method of claim 11, wherein the tissue-attachment portion comprises a shape-memory alloy that is configured to assume a U-shape when the tissue-attachment portion is in the attachment configuration.

13. The method of claim 10, wherein withdrawing the delivery device from the collapsible portion of the hole-closure device comprises withdrawal of the shaft from within the collapsible portion such that the collapsible portion inwardly collapses from the expanded state to the collapsed state.

14. A method for closing a hole in cardiac tissue comprising:
positioning an apparatus configured to close a hole in cardiac tissue within the hole such that a collapsible structure of the apparatus, in an expanded state, extends through the hole;
engaging a tissue-attachment portion of the apparatus with the cardiac tissue that surrounds the hole, the tissue-attachment portion being coupled to the collapsible structure; and
transitioning the collapsible structure from the expanded state to a collapsed state for closing the hole in the cardiac tissue, wherein collapsing the collapsible structure causes the tissue-attachment portion to draw the cardiac tissue together to close the hole.

15. The method of claim 14, wherein positioning the apparatus includes inserting a delivery device into the hole with the apparatus being disposed around the delivery device such that the collapsible structure is held in the expanded state thereby.

16. The method of claim 15, wherein the delivery device includes a sheath and the tissue-attachment portion of the apparatus is configured to be in a delivery configuration thereof when the sheath is disposed around the tissue-attachment portion, and in an attachment configuration thereof when the sheath is not disposed around the tissue-attachment portion.

17. The method of claim 16, further comprising withdrawing the sheath of the delivery device relative to the tissue-attachment portion of the apparatus to permit the tissue-attachment portion to transition from the delivery configuration to the attachment configuration for engaging the tissue-attachment portion with the cardiac tissue.

18. The method of claim 17, wherein the tissue-attachment portion comprises a shape-memory alloy and is configured to assume a U-shape when the tissue-attachment portion is in the attachment configuration.

19. The method of claim 15, wherein the delivery device includes a shaft configured to maintain the collapsible structure of the apparatus in the expanded state by extending therethrough, and wherein transitioning the collapsible structure from the expanded state to the collapsed state comprises withdrawing the shaft of the delivery device from within the collapsible portion such that the collapsible portion inwardly collapses from the expanded state to the collapsed state.

20. The method of claim 19, wherein the collapsible structure includes a sealing material disposed in an interior thereof and wherein collapse of the collapsible structure causes the sealing material to seal a center of the apparatus.

* * * * *